(12) United States Patent
Williams et al.

(10) Patent No.: US 7,357,509 B2
(45) Date of Patent: Apr. 15, 2008

(54) METRICS TO PREDICT SUBJECTIVE IMPACT OF EYE'S WAVE ABERRATION

(75) Inventors: David R. Williams, Fairport, NY (US); Raymond A. Applegate, Kingwood, TX (US); Larry N. Thibos, Bloomington, IN (US)

(73) Assignees: University of Rochester, Rochester, NY (US); University of Houston, Houston, TX (US); Indiana University, Bloomington, IN (US)

( * ) Notice: Subject to any disclaimer, the term of this patent is extended or adjusted under 35 U.S.C. 154(b) by 593 days.

(21) Appl. No.: 10/833,277

(22) Filed: Apr. 28, 2004

(65) Prior Publication Data

US 2004/0263786 A1 Dec. 30, 2004

Related U.S. Application Data

(60) Provisional application No. 60/465,804, filed on Apr. 28, 2003.

(51) Int. Cl.
*A61B 3/00* (2006.01)
(52) U.S. Cl. .................. 351/246; 351/200; 351/212
(58) Field of Classification Search ............... 351/246
See application file for complete search history.

(56) References Cited

U.S. PATENT DOCUMENTS

| | | | |
|---|---|---|---|
| 6,095,651 A * | 8/2000 | Williams et al. ........... 351/246 |
| 6,338,559 B1 | 1/2002 | Williams et al. | |
| 6,460,997 B1 * | 10/2002 | Frey et al. .................. 351/211 |
| 6,511,180 B2 | 1/2003 | Guirao et al. | |
| 6,634,751 B2 | 10/2003 | Turner et al. | |
| 6,722,767 B2 | 4/2004 | Dick et al. | |
| 6,761,454 B2 | 7/2004 | Lai et al. | |
| 6,817,714 B2 * | 11/2004 | Altmann ..................... 351/177 |
| 6,964,480 B2 * | 11/2005 | Levine ....................... 351/211 |
| 7,077,522 B2 | 7/2006 | Williams | |
| 2002/0167643 A1 | 11/2002 | Youssefi | |
| 2003/0038921 A1 | 2/2003 | Neal et al. | |
| 2003/0076478 A1 | 4/2003 | Cox | |
| 2005/0134799 A1 * | 6/2005 | Thompson et al. ......... 351/222 |

OTHER PUBLICATIONS

Williams, D.R. Assessment of Optical Aberrrations of the Eye: Wavefront Sensing and Adaptive Optics., ARVO, Ft. Lauderdale, FL, May 2002.
Williams, D.R. Subjective Image Quality Metrics from the Wave Aberration. 4th International Congress of Wavefront Sensing and Aberration-Free Refractive Correction, San Francisco, CA, Feb. 16, 2003.
Williams, D.R. Predicting Subjective Image Quality from the Wave Aberration. ASCRS, San Francisco, CA, Apr. 12, 2003.

* cited by examiner

*Primary Examiner*—Jessica T Stultz
(74) *Attorney, Agent, or Firm*—Blank Rome LLP

(57) ABSTRACT

Several metrics to predict the subjective impact of the eye's wavefront aberrations are presented. The metrics can be based on RMS wavefront errors or slopes, the area of the critical pupil, a curvature parameter, the point spread function, the optical transfer function, or the like. Other techniques include the fitting of a sphero-cylindrical surface, the use of multivariate metrics, and customization of the metric for patient characteristics such as age.

1 Claim, 15 Drawing Sheets

Figure 2
2nd
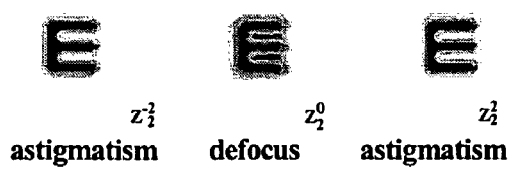
$z_2^{-2}$     $z_2^0$     $z_2^2$
astigmatism   defocus   astigmatism
3rd
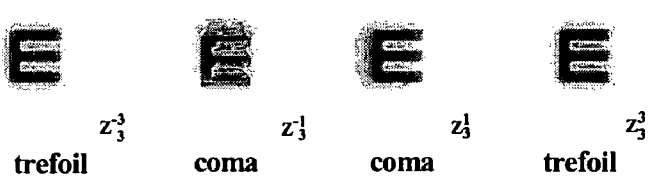
$z_3^{-3}$     $z_3^{-1}$     $z_3^1$     $z_3^3$
trefoil    coma    coma    trefoil
4th
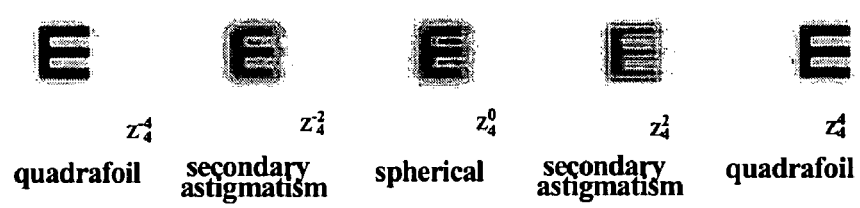
$z_4^{-4}$    $z_4^{-2}$    $z_4^0$    $z_4^2$    $z_4^4$
quadrafoil   secondary astigmatism   spherical   secondary astigmatism   quadrafoil
5th
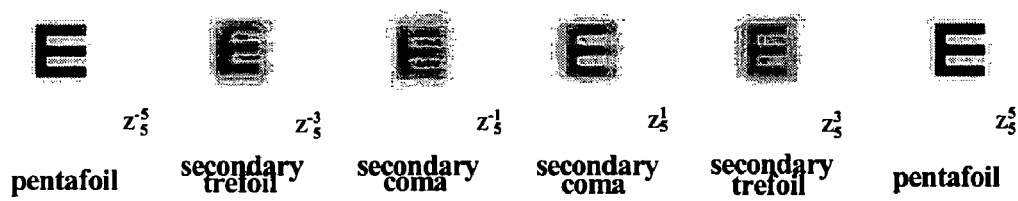
$z_5^{-5}$   $z_5^{-3}$   $z_5^{-1}$   $z_5^1$   $z_5^3$   $z_5^5$
pentafoil   secondary trefoil   secondary coma   secondary coma   secondary trefoil   pentafoil Defocus
rms = 0.25 μm Spherical
Aberration
rms = 0.14 mm Defocus and
Spherical Aberration
rms = 0.287 mm Sharpness = Total intensity in weighted PSF

METRICS TO PREDICT SUBJECTIVE IMPACT OF EYE'S WAVE ABERRATION

REFERENCE TO RELATED APPLICATION

The present application claims the benefit of U.S. Provisional Application No. 60/465,804, filed Apr. 28, 2003, whose disclosure is hereby incorporated by reference in its entirety into the present disclosure.

STATEMENT OF GOVERNMENT INTEREST

The present invention was supported in part by NIH grants EY R01 08520 and EY R01 5109. The government has certain rights in the invention.

BACKGROUND OF THE INVENTION

1. Field of the Invention

This invention relates to metrics of the quality of vision using wave front sensing and/or knowledge of the visual system. This invention particularly relates to new metrics for optical performance and a set of metrics correlated with visual performance.

2. Background of the Art

The advent of rapid, automated wave front sensing in the eye now provides the clinician with a much richer description of the optics of each patient's eye than has been available before. Numerous methods have been developed to measure the wave aberration, some of which are objective, such as the Shack-Hartmann wave front sensor, while others are subjective, such as the spatially resolved refractometer. In either case, these devices measure only optical characteristics of the eye. This is all that is required for some applications such as correcting the optics of the eye for imaging the retina. But in the case of correcting the optics of the eye for improving vision, neural processing as well as optical image formation is also important. As the technology for measuring the wave aberration matures, there is a need to discover better ways of using wave aberration measurements to improve vision. A key issue is how to transform the wave aberration into a succinct description of how it will affect the patient's vision.

The ability to predict the visual impact of a given wave aberration is important for several reasons. First, this information can be used to evaluate quality of vision and expected visual performance. Such information could be used in screening individuals for driver's licenses, disability claims, or evaluating quality of life issues such as the ability to recognize faces. Second, a metric derived from the wave aberration can guide the clinician in selecting the best strategy for improving vision in each patient. For example, are the higher order aberrations in the patient's wave aberration severe enough to warrant customized refractive surgery, or is she likely to benefit just as much from conventional refractive surgery? If the patient is complaining of haloes, flares, monocular diplopia, or other visual defects, can the problem be linked to the eye's optical performance, is the patient unusually sensitive to small defects in vision, or are other neural factors implicated? Third, metrics to predict the subjective impact of the wave aberration can be incorporated into algorithms to compute the best vision correction given a particular wave aberration. Methods of vision correction such as contact lenses, spectacles, and refractive surgery generally correct fewer aberrations than can be measured with wave front sensing technology. For example, spectacles can correct only prism, sphere, and cylinder whereas wave front sensors can reliably measure tens or even hundreds of aberrations in normal human eyes. The higher order aberrations can influence the values of defocus and astigmatism that provide the best subjective image quality. The development of metrics for subjective image quality that include the effects of higher order aberrations will allow the optimization of vision correction.

The common practice today is to rely on the patient's responses to refract the eye. These measurements are time-consuming with a typical subjective refraction taking several minutes per eye to perform. A wave front sensor measurement can be performed in a matter of seconds. A conventional subjective refraction involves adjusting three aberrations (sphere cylinder and axis) simultaneously to optimize visual performance. However, wave front technology allows many more than three aberrations to be corrected. A subjective procedure to identify the best values of more than three aberrations is not practical. For this reason, higher order corrections must depend on algorithms to optimize vision rather than on the subjective response of the patient. Moreover, conventional refraction is subject to the variability in the patient's response. If an objective metric could be developed that adequately mimics the behavior of the average visual system, one can average the results of multiple objective measurements in the time it takes to perform a single subjective refraction, reducing the variability in the correction and achieving a better visual outcome.

The role of individual aberrations in visual performance. Just as the conventional refraction can be decomposed into prism, sphere, cylinder, and axis, "irregular astigmatism" can be broken into individual aberrations, or Zernike modes, with a process called Zernike decomposition. Zernike decomposition can provide valuable insight into the relative importance of different aberrations for vision. It is useful in diagnosing the cause of a particular wave aberration as well as visual complaints. For example, a refractive surgery patient who presents post-operatively with an increase of vertical coma and complains of a vertical flare on car headlights at night very likely suffered some vertical decentration during laser ablation.

The evaluation of individual Zernike modes reveals large differences in their subjective impact. Applegate et al. (2002) created modified (or "aberrated") log MAR acuity charts by convolving the image on a standard chart with the point spread functions (PSF) corresponding to individual Zernike modes. The visual impact of each Zernike mode in $2^{nd}$ through $4^{th}$ radial order was studied. A fixed level of RMS error (0.25 μm over a 6 mm pupil—a dioptric equivalent of 0.19 D) was used in each case. Subjects with 20/15 or better visual acuity and best corrected vision were asked to read each of the aberrated charts. The total number of letters read correctly up to the fifth miss were recorded for each chart. The number of letters lost was calculated by subtracting the number of letters read correctly for a perfect (unaberrated) chart. FIG. 1 shows the number of high contrast letters lost as a function of Zernike Mode. Note that more letters are lost for modes in the middle of a given Zernike order than those at either the beginning or the end of each order. For example, in the second radial order, defocus (labeled 4 in the figure) degrades performance more than either astigmatism mode (3 and 5). Similarly in the third radial order, coma (modes 7 and 8) decreases acuity more than trefoil (modes 6 and 9). Despite the fact that the total aberration as expressed by RMS error was constant, acuity varied by up to 10 letters (2 lines) depending on which Zernike mode contained the wave front aberration. FIG. 2 shows a simulation that captures the essence of Applegate's conclusion. The letter E at a size corresponding to (20/40) has been convolved with the PSF corresponding to each Zernike mode. The RMS wave front error of each Zernike mode was fixed at 0.25 microns. Wavelength was 555 nm and the pupil size was 6 mm. FIG. 3 shows the corresponding Zernike modes for comparison. Note that the letters at the center of the pyramid are more blurred than those along the flanks. Inspection of the original modes in FIG. 3 shows why this is true. The flanking modes share the common feature that the wave aberration is flat (uniform gray in the figure) over much of the pupil. The light that passes through these regions of the pupil will form sharp images on the retina. The aberrations that blur strongly, on the other hand, tend to have nonzero slope over a larger contiguous fraction of the pupil.

Chen and Williams obtained similar results to those of Applegate et al (2002), using a deformable mirror to produce aberrations instead of using the MAR acuity charts, modified by image processing convolution with the point spread functions. They used the deformable mirror to blur the subject's vision with a single Zernike mode, one at a time, while all other aberrations were corrected across a 6 mm pupil. The subject adjusted the coefficient associated with this Zernike mode to produce an amount of blur that equaled a standard amount of blur. They also found that aberrations in the center of the pyramid blurred more than those at the edge, and that this was true for $5^{th}$ order aberrations as well as 2, 3, and $4^{th}$. See FIG. 3 to see which modes belong to each order.

The Problem with Zernike Decomposition. By analogy with the success in chemistry of reducing molecules to their atomic constituents, it is tempting to think that reducing the wave aberration to its fundamental components might provide the path to subjective image quality. However, experiments cast doubt on the value of this reductionist approach because Zernike modes can interact strongly with each other to determine final image quality. Their subjective effects do not add together in a simple way as illustrated in FIG. 4. Shown are the retinal images of the letter E for three hypothetical eyes, one suffering only from defocus, one suffering from spherical aberration, and one suffering from both defocus and spherical aberration in the same amounts as present in the first two eyes. (In the usual practice to describe the effect of multiple aberrations, it is the variance, which is the RMS squared, which is added, not the RMS itself. For example, in this case $0.25^2+0.14^2=0.287^2$). Strikingly, the image quality is obviously best in the eye that suffers from both aberrations rather than the eyes that suffer from only one of them. Consistent with this demonstration, Applegate et al. (2003) have measured the interactions between Zernike modes and found that pairs of aberrations can sometimes increase acuity more than would be expected from the individual components or they can sometimes lead to a larger reduction in acuity than expected (Applegate et al., 2003). Modes two radial orders apart and having the same sign and angular frequency (e.g., $C_2^0+C_4^0$) tend to combine to increase visual acuity compared to loading the same magnitude RMS error into either component individually. Modes within the same radial order (e.g., $C_4^{-4}+C_4^0$) tend to combine to decrease acuity compared to loading the same magnitude RMS error into either component individually. The complexity of the interactions between Zernike modes in subjective blur means that Zernike decomposition is unlikely to be a productive avenue for deriving a metric of subjective image quality. However, our visual quality metric derived from wavefront and visual processing can predict subjective image quality (Marsack et al 2004).

SUMMARY OF THE INVENTION

It is therefore an object of the invention to provide improved metrics for predicting the subjective impact of the eye's wavefront aberrations. The metrics can be based on RMS wavefront errors or slopes, the area of the critical pupil, a curvature parameter, the point spread function, the optical transfer function, or the like. Other techniques include the fitting of a sphero-cylindrical surface, the use of multivariate metrics, and customization of the metric for patient characteristics such as age.

The goal is to be able to take measurements of the wavefront aberrations of the eye and to provide metrics that predict visual performance. Such metrics would be functions of the wavefront aberrations or of the wavefront aberrations and the neural transfer function.

The following works are related to the present invention and are hereby incorporated by reference in their entireties into the present disclosure:

R. Applegate, "Wavefront Sensing, Ideal Corrections and Visual Performance," *Optometry and Visual Science* 81 (3), March, 2004.

L. Thibos, "Determining Sphero-cylindrical Corrections from Wave Aberrations," 5th International Congress of Wavefront Sensing & Optimized Refractive Corrections, Feb. 21-23, 2004, Whistler, British Columbia, Canada.

L. Thibos et al, "Objective Estimates of Subjective Refraction from Wavefront Aberration Maps," ARVO, Apr. 27, 2004.

Williams et al, U.S. Pat. No. 6,511,180.

Applegate, R A, Sarver, E J, Khemsara, V, "Are All Aberrations Equal?" *Journal of Refractive Surgery*, 18:S556-S562, 2002.

Applegate, R A, Marsack, J, Ramos, R, Sarver, E J, "Interaction Between Aberrations Can Improve or Reduce Visual Performance," *J Cataract and Refractive Surgery*, 29:1487-1495, 2003.

Marsack, J, Thibos, L N, Applegate, R A, "Metrics of Optical Quality Derived from Wave Aberration Predict Visual Performance," *Journal of Vision*, 4, 322-328 (2004).

Thibos, L N, Hong, X, Bradley, A, Applegate, R A, "Accuracy and Precision of Objective Refraction from Wavefront Aberrations," *Journal of Vision*, 4, 329-351 (2004).

BRIEF DESCRIPTION OF THE DRAWINGS

Preferred embodiments of the present invention will be set forth in detail with reference to the drawings, which show the following:

FIG. 2. Image simulations of the impact of 0.25 micrometers of RMS error for the individual modes of the Zernike expansion through the $5^{th}$ radial order over a 6 mm pupil, $\lambda$=555 nm. Notice that modes in the center of the pyramid have bigger effect than modes along the edge of the pyramid.

DETAILED DESCRIPTION OF THE PREFERRED EMBODIMENTS

Figure 1:
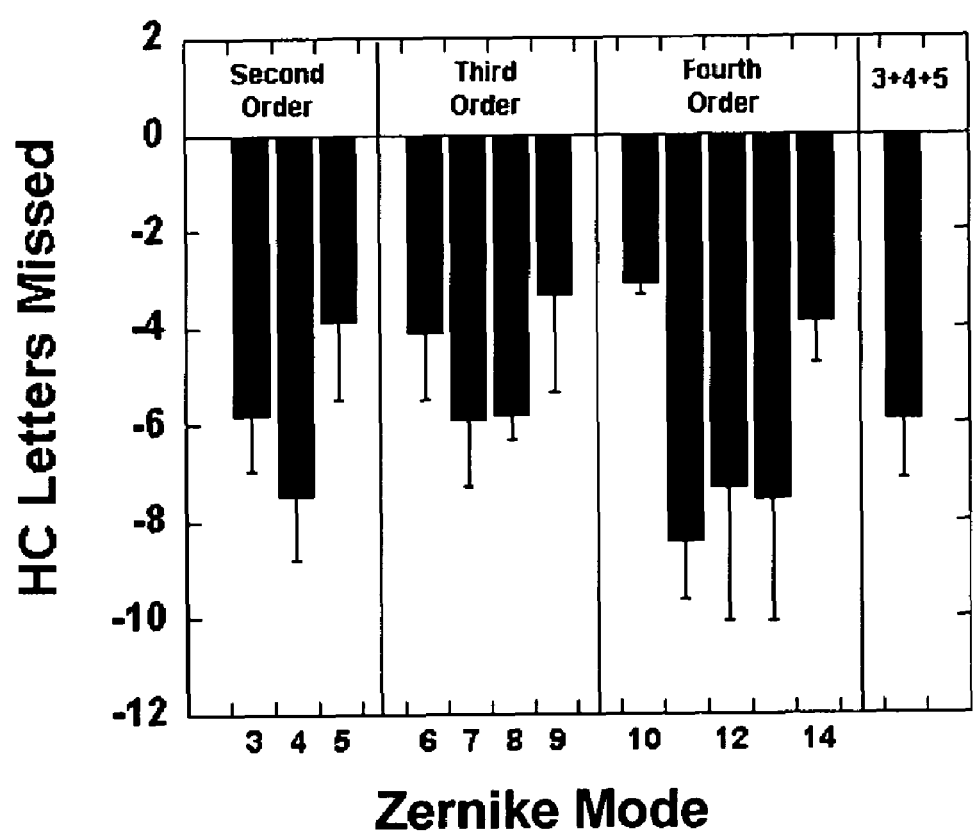
FIG. 1. Average high contrast letters missed as a function of Zernike mode. The far right panel of each graph (labeled 3+4+5) displays the result for the experimental chart where the rms error was equally distributed across $C_2^{-2}$, $C_2^0$, $C_2^2$ (sphere and cylinder modes) such that the total rms error was 0.25 micrometers over a 6 mm pupil, $\lambda$=555 nm. Error bars are 1 SD.
Figure 3:
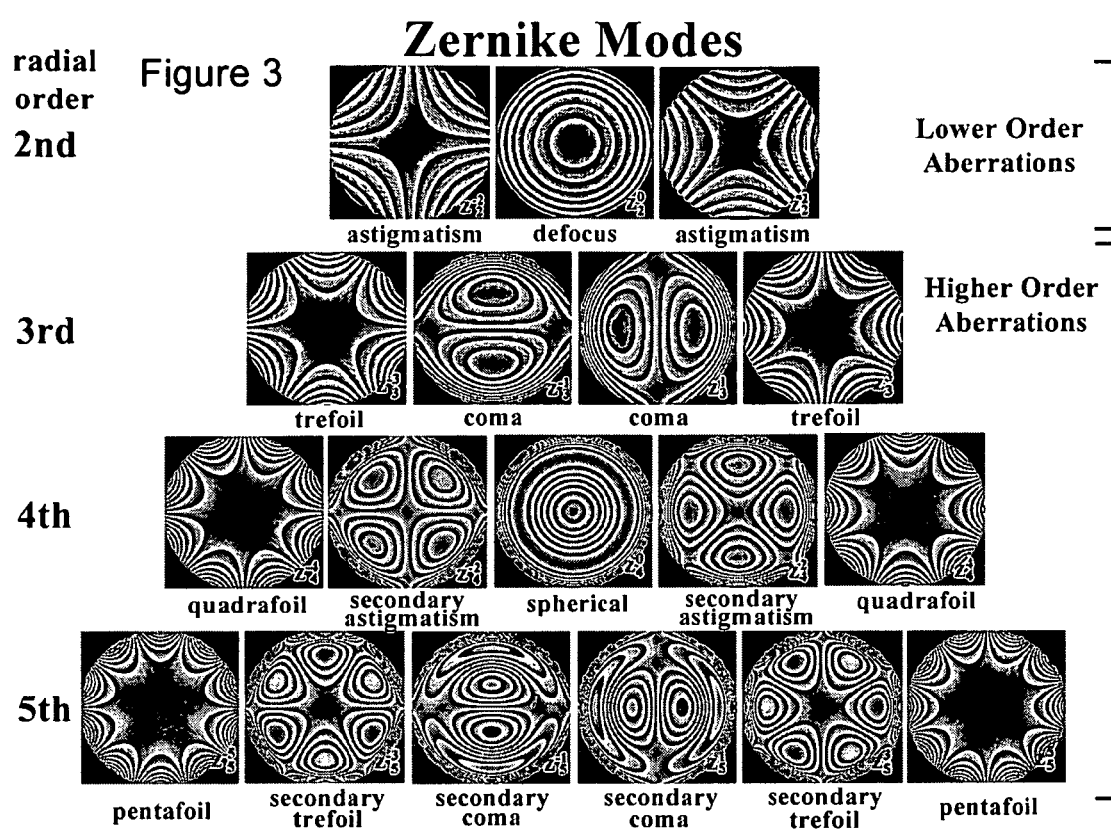
FIG. 3. Wave front error for Zernike modes through the $5^{th}$ radial order. (6 mm pupil, $\lambda$=555 nm).

Various preferred embodiments of the present invention will be set forth in detail with reference to the drawings, in which like reference numerals refer to like elements or steps throughout.

Image Quality Metrics

Figure 4:
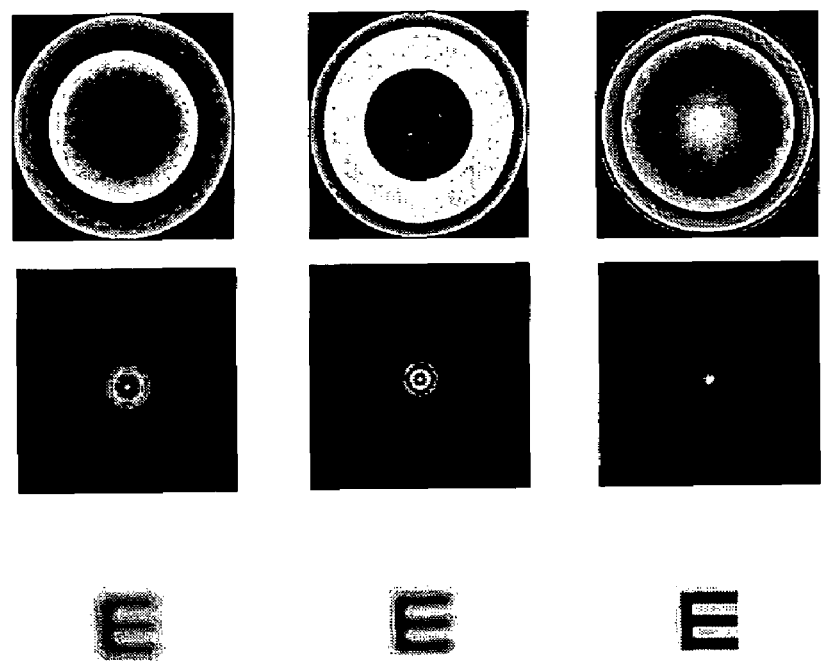
FIG. 4. The interaction between defocus and spherical aberration. Each column represents a hypothetical eye with wave aberration over a 6 mm pupil, a PSF at 555 nm, viewing a 20/40 letter. The left column shows an eye suffering only from defocus at 0.25 µm rms. The middle column shows an eye suffering only from spherical aberration at 0.14 µm rms. The right column shows an eye suffering from both spherical aberration and defocus in the same amounts as in the other two eyes, for a total rms of 0.287 µm. The eye on the right has the best image quality even though the RMS Wave front Error is the highest.
Figure 5:
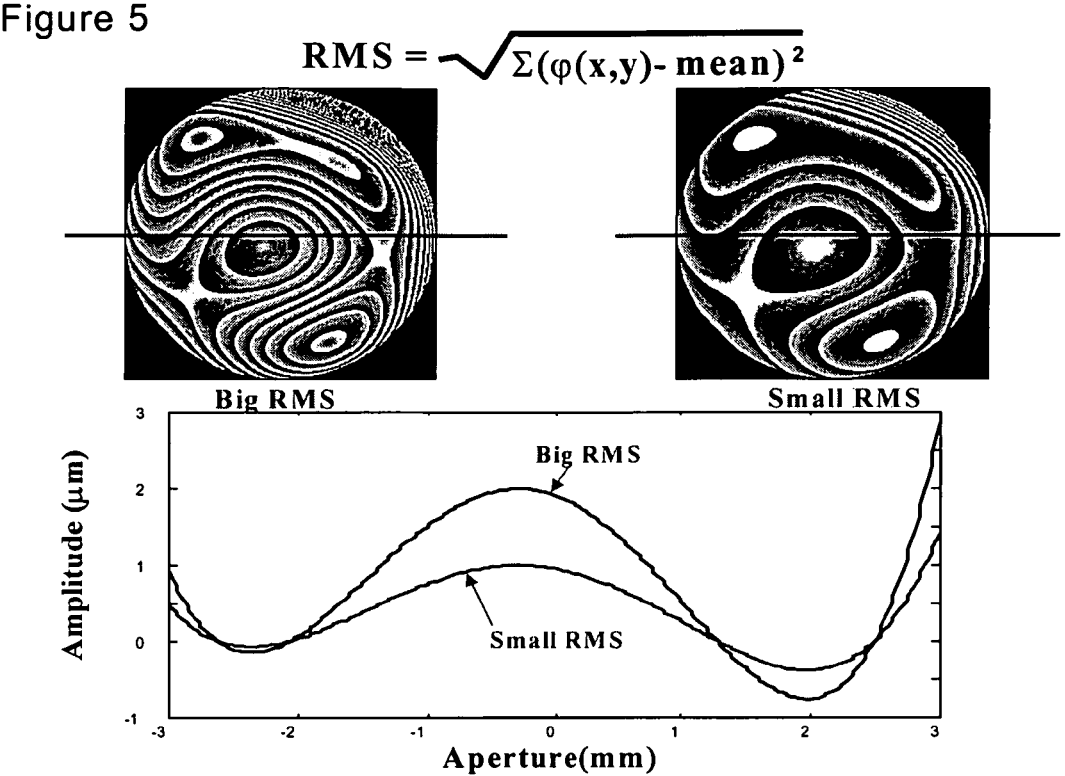
FIG. 5. RMS wave front error is a pupil-plane measure of optical quality that is equal to the square root of wave front variance. The contour map at the left indicates a relatively large RMS error whereas the contour map at the right indicates a relatively small wave front error. The bottom graph shows the amplitude of wave front error for a horizontal trace across the pupil.

Pupil Plane Metrics using Conventional Wavefront Description: Currently, the most commonly used metric is the RMS Wave front Error, defined as the square root of the sum of the squares of the deviation of the actual wave front from the ideal wave front (see FIG. 5). This is the same as the standard deviation of the wave aberration. Unfortunately, RMS Wave front Error is not an especially useful metric for describing the subjective impact of the eye's wave aberration. For example, FIG. 4 shows that the eye with the best image quality can sometimes have the highest RMS. This is because metrics defined in the pupil plane, such as RMS, do not take into account the interaction of light entering through different parts of pupil as they form the retinal image. Moreover, the retinal image is processed by neural stages that are not incorporated in pupil plane metrics.

Several pupil plane metrics using conventional wave front descriptors are given below:

WF1=RMS of wave front error computed over the whole pupil (microns)

$$WF1 = \left[ \frac{1}{\text{pupil area}} \int_{pupil} (w(x,y) - \overline{w})^2 dxdy \right]^{0.5}$$

where w(x,y) is the wave front aberration function.

WF2=peak-to-valley difference (microns)

$$WF2 = \max(w(x,y)) - \min(w(x,y))$$

WF3=RMS of wave front slope computed over the whole pupil (arcmin)

$$WF3 = RMS_s$$
$$= \left[ \frac{1}{A} \int_{pupil} (w_x(x,y) - \overline{w}_x)^2 + (w_y(x,y) - \overline{w}_y)^2 dxdy \right]^{0.5}$$

where $w_x = dw/dx$; $w_y = dw/dy$ is the gradient of w(x,y), and A=pupil area.

Figure 6:
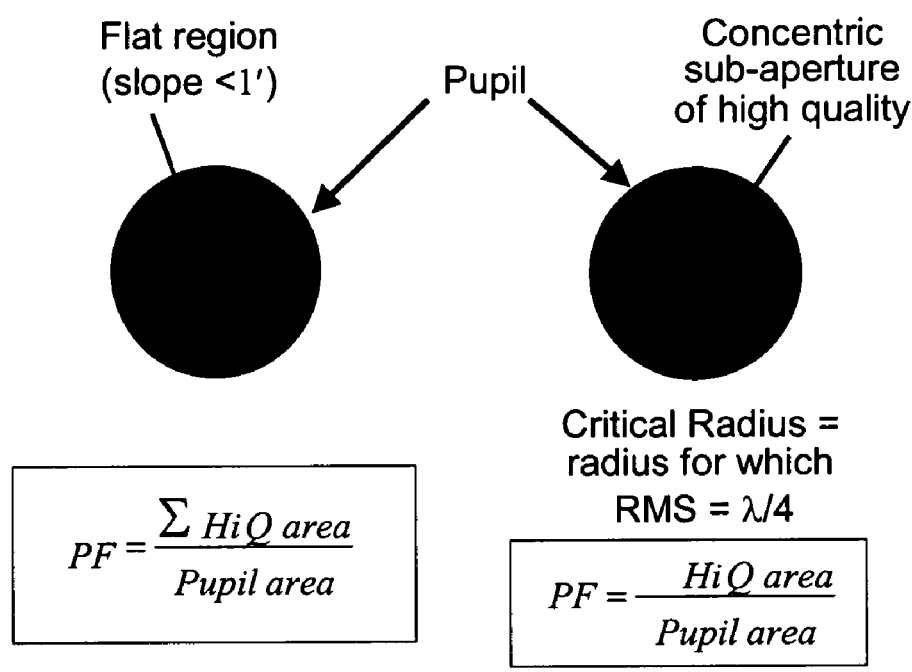
FIG. 6. Two methods for determining Pupil Fraction (PF). In the left diagram, we compute the total amount of pupil area for which the slope of the wave front aberration function is less than some criterion (e.g. 1 minute of arc) and divide the result by pupil area. In the right diagram, we compute the area of that sub-aperture for which the total RMS error is less than some criterion (e.g. ¼ wavelength of light) and divide the result by pupil area.

Pupil Plane Metrics with a Pupil Fraction Parameter A better pupil plane metric, called Pupil Fraction, quantifies what fraction of the eye's pupil has good optical quality. It is equal to the fraction of pupil area for which optical quality is reasonably good. There are many ways to locate the portion of the pupil that is optically good. For example, one criterion is to chose the concentric area of the pupil in which the RMS Wave front Error is less than some criterion, such as λ/4 wavelengths of light, as illustrated in FIG. 6. Another method, suggested by Stan Klein, is based on wave front slope. Regardless of which method is used, a large Pupil Fraction is preferred because it means that most of the light entering the pupil is used to form a high-quality retinal image.

Several pupil plane metrics using a pupil fraction parameter are shown below. Note that these metrics are normalized such that the range of possible values is 0-1.

WF4=pupil fraction when critical pupil is defined as the concentric area for which RMS wave front error<some criterion (e.g. $\lambda/4$)

$$WF4 = \frac{\text{Area of critical pupil}}{\text{Area of pupil}}$$

WF5=pupil fraction when critical pupil is defined as the concentric area for which the absolute value of wave front error<some criterion (e.g. $\lambda/4$)

$$WF5 = \frac{\text{Area of critical pupil}}{\text{Area of pupil}}$$

WF6=pupil fraction when critical pupil is defined as the concentric area for which the magnitude of wave front slope<some criterion (e.g. 1 arcmin)

$$WF6 = \frac{\text{Area of critical pupil}}{\text{Area of pupil}}$$

In any metric based on pupil fraction, the critical pupil can be replaced by the tellelated pupil, which, instead of a concentric sub-aperture, is an aggregation of all locations in the pupil.

Figure 7:
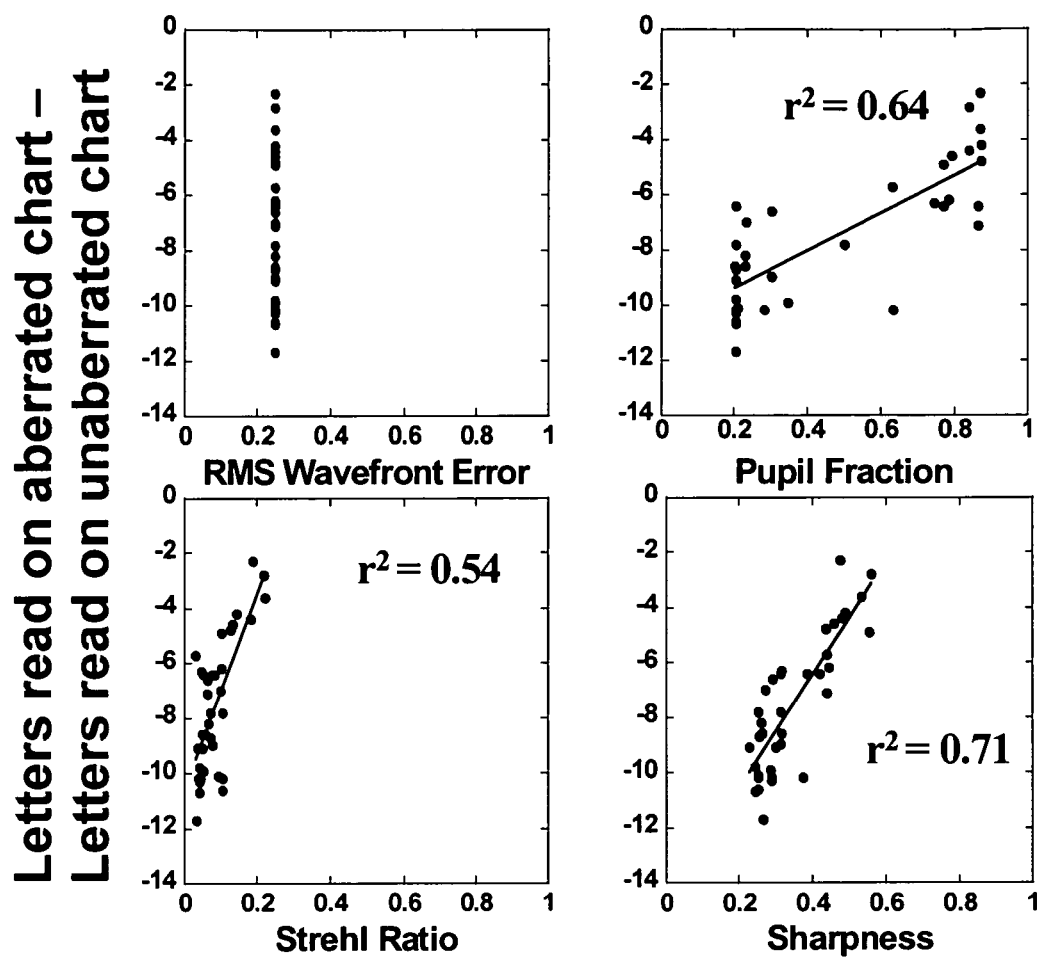
FIG. 7. Different image quality metrics have different ability to predict the loss of visual performance caused by optical aberrations.

In one experiment, a Pupil Fraction metric (WF4) accounted for 64% of the variance in acuity whereas the conventional RMS metric (WF1) could not account for any of the variation in acuity because RMS was intentionally held constant (FIG. 7). Pupil Fraction was also an effective metric for calculating subjective refraction in the Indiana aberration study.

Pupil Plane Metrics with a Curvature Parameter The reason for developing a wavefront metric based on local wavefront curvature is that curvature is a fundamental property of wavefronts that determines how wavefronts propagate and form images. If all points on a wavefront have exactly the same curvature, that wavefront has a perfect spherical shape that will focus down to a perfect image. To the contrary, variations in curvature will lead to imperfections in the image.

The two additional metrics are extensions of the concepts that led to metrics WF3 and WF6 in which wavefront slope replaces wavefront curvature. Curvature is more complicated to specify than slope, which in turn is more complicated than wavefront phase. Thus, curvature varies not only with location of the wavefront within the pupil plane, but also varies with meridian for any given point on the wavefront. Nevertheless, it is possible to define the mean curvature $\kappa$ at any given point by averaging the principal curvatures. The extent to which $\kappa$ varies across the pupil is a measure of image quality. Low variation means good quality. refinements of this metric would take account of the variation of curvature with meridian.

So here are the curvature metrics:
WF7=RMS of wavefront curvature computed over the whole pupil (arcmin)

$$WF7 = 0.5 \int_{pupil} (\kappa(x, y) - \bar{\kappa})^2 dx dy$$

where $\kappa(x,y)$ is the mean curvature of the wavefront as a function of pupil location.

WF8=pupil fraction when critical pupil is defined as the aggregate of all pupil locations for which the magnitude of wavefront curvature<some criterion (e.g. 0.1 Diopters)

$$WF8 = \frac{\text{Area of critical pupil}}{\text{Area of pupil}}$$

Again, the tesselated pupil can be used instead.

Another metric based on curvature is the average blur strength, which can be expressed in diopters. To compute the blur-strength map we first use the principal curvature maps to compute the astigmatism map:

$$J(x, y) = \frac{k_1(x, y) - k_2(x, y)}{2}$$

and then combine the astigmatism map with the mean curvature map using the Pythagorean formula to produce a blur strength map:

$$B(x, y) = \sqrt{M^2(x, y) + J^2(x, y)}$$

The spatial average of this blur strength map is a scalar value that represents the average amount of focusing error in the system that is responsible for image degradation, $B_{ave}$=average blur strength (diopters):

$$B_{ave} = \frac{1}{\text{pupil area}} \int_{pupil} B(x, y) dx dy$$

Blur strength can be used to compute pupil fraction by either the concentric pupil or tessellation methods.

Image Plane Metrics using the Point Spread Function: Image plane metrics are computations performed on the retinal image rather than directly on the wave aberration. These metrics have the advantage that they take into account the interaction of light entering different parts of the pupil. The wave aberration measured by a wave front sensor remains the input to the process, but image plane metrics incorporate the computations that transform the wave aberration into the retinal image.

In optics, there are two general strategies for describing the quality of an imaging system, one based on the image formed of a point of light, like a star, and another based on the image formed of a set of sine wave gratings. These two descriptions turn out to be exactly equivalent to one another in terms of the information they contain, though often the description based on gratings is easier to compute. Of course, the visual environment is composed of many objects that are more interesting to people than points of light and gratings. However, it is possible to compute the retinal image of any object once the image of a point or the images of a number of gratings is known. The intuition behind the computation based on the PSF (convolution) is that any object can be thought of as a collection of points of light, each of which produces its own blurred image. The retinal image of the object is then the sum of all these blurred images, one from each point in the object. Similarly, the object can be described as the sum of many sine wave gratings each of which produces a sine wave grating in the retinal image that is reduced in contrast (reduced modulation) and shifted in location (phase shift). These contrast reductions and phase shifts completely describe the optical quality of the eye and contain exactly the same information as the point spread function.

Figure 8:
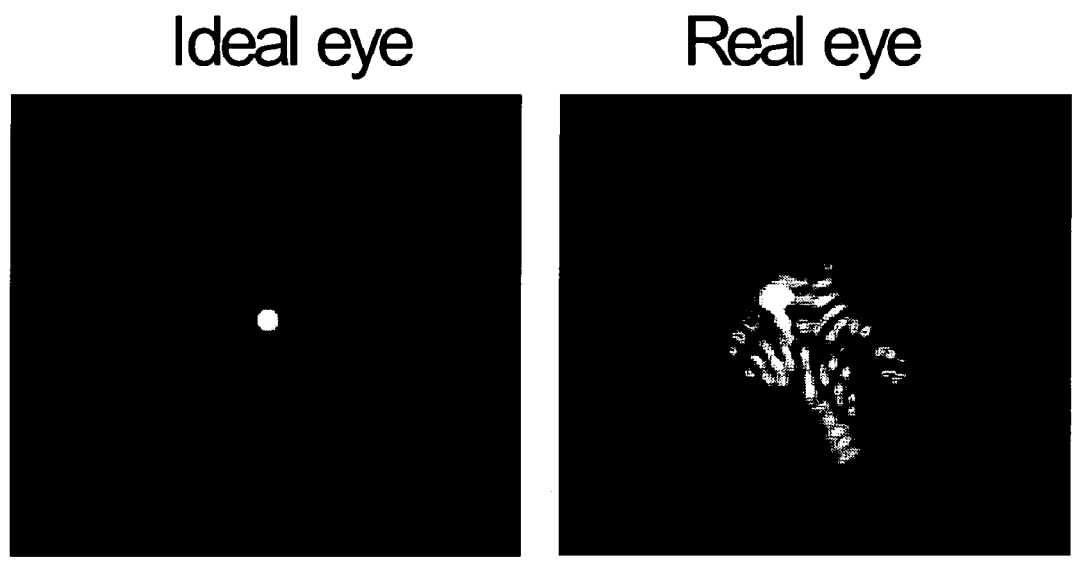
FIG. 8. PSF examples for an eye that has no aberrations and is blurred only by diffraction (left, 6 mm pupil, 555 nm) and a typical PSF from a normal eye (right). The real eye light distribution is extremely complicated in its structure and the challenge for making a metric of image quality is to reduce this distribution to a single number that best captures its visual impact.

FIG. 8 shows examples of a typical PSF from a normal eye compared with the ideal PSF from an eye that has no aberrations and is blurred only by diffraction. The light distribution for the real eye is extremely complicated in its structure and the challenge is to reduce this distribution to a single number that best captures its visual impact. The goal of an ideal correction is to redirect the light so that it is concentrated as much as possible into a single spot. This will increase the compactness of the PSF, which increases its intensity at the center, and also reduces asymmetries. Point spread function metrics are attempts to capture these aspects of a good PSF with a single number.

Several image plane metrics, which use the PSF, the Point Spread Function, are given below:

PS1=diameter of a circular area centered on peak which captures 50% of the light energy (arcmin);

PS1=r, where r is defined implicitly by:

$$\int_0^{2\pi}\int_0^r PSF_N(r,\theta) r\, dr\, d\theta = 0.5$$

where $PSF_N$ is the normalized (i.e. total intensity=1) point-spread function centered on the origin (i.e. peak of $PSF_N$ is at r=0).

PS2=equivalent width of centered PSF (arcmin)

$$PS2 = \frac{\int_{-\infty}^{\infty}\int_{-\infty}^{\infty} PSF(x,y)\,dx\,dy}{PSF(x_0, y_0)}$$

where $x_0, y_0$ are the coordinates of the peak of the PSF.

PS3=square root of second moment of light distribution (arcmin)

$$PS3 = \left[\frac{\int_{-\infty}^{\infty}\int_{-\infty}^{\infty}(x^2+y^2)PSF(x,y)\,dx\,dy}{\int_{-\infty}^{\infty}\int_{-\infty}^{\infty}PSF(x,y)\,dx\,dy}\right]^{0.5}$$

PS4=half width at half height (arcmin)

$$PS4 = \left[\frac{1}{\pi}\int_{-\infty}^{\infty}\int_{-\infty}^{\infty}B(x,y)\,dx\,dy\right]^{0.5}$$

where B(x,y)=1 if PSF(x,y)>max(PSF)/2, otherwise B(x,y)=0.

PS5=correlation width of light distribution (arcmin)

$$PS5 = \left[\frac{1}{\pi}\int_{-\infty}^{\infty}\int_{-\infty}^{\infty}B(x,y)\,dx\,dy\right]^{0.5}$$

where B(x,y)=1 if PSF⊗PSF>max(PSF⊗PSF)/2, otherwise B(x,y)=0. In this expression, PSF⊗PSF is the autocorrelation of the PSF.

PS6=Strehl ratio computed in spatial domain $$PS6 = \frac{\max(PSF)}{\max(PSF_{DL})}$$

where $PSF_{DL}$ is the diffraction-limited PSF for the same pupil diameter.

PS7=light-in-the-bucket (percentage of total energy falling in diffraction core)

$$PS7 = \int_{DL\ core} PSF_N(x,y)\,dx\,dy$$

where $PSF_N$ is the normalized (i.e. total intensity=1) point-spread function. The domain of integration is the central core of a diffraction-limited PSF for the same pupil diameter.

PS8=standard deviation of light distribution, normalized to diffraction limited value $$PS8 = \frac{\left[\frac{1}{\text{pupil area}}\int_{pupil}(PSF(x,y)-\overline{PSF})^2\,dx\,dy\right]^{0.5}}{\left[\frac{1}{\text{pupil area}}\int_{pupil}(PSF_{DL}(x,y)-\overline{PSF_{DL}})^2\,dx\,dy\right]^{0.5}}$$

where $PSF_{DL}$ is the diffraction-limited point-spread function.

PS9=entropy $$PS9 = -\int_{-\infty}^{\infty}\int_{-\infty}^{\infty} PSF(x,y)\ln(PSF(x,y))\,dx\,dy$$

PS10=sharpness, normalized to the sharpness value for a diffraction-limited point-spread function.

$$PS10 = \frac{\int_{-\infty}^{\infty}\int_{-\infty}^{\infty} PSF(x,y)G(x,y)\,dx\,dy}{\int_{-\infty}^{\infty}\int_{-\infty}^{\infty} PSF_{DL}(x,y)G(x,y)\,dx\,dy}$$

where G is a bivariate Gaussian weighting function.

PS11=visual Strehl ratio computed in spatial domain $$PS11 = \frac{\int_{-\infty}^{\infty}\int_{-\infty}^{\infty} PSF(x, y)N(x, y)dxdy}{\int_{-\infty}^{\infty}\int_{-\infty}^{\infty} PSF_{DL}(x, y)N(x, y)dxdy}$$

where N is a bivariate neural weighting function equal to the inverse Fourier transform of the neural contrast sensitivity function for interference fringes.

Figure 9:
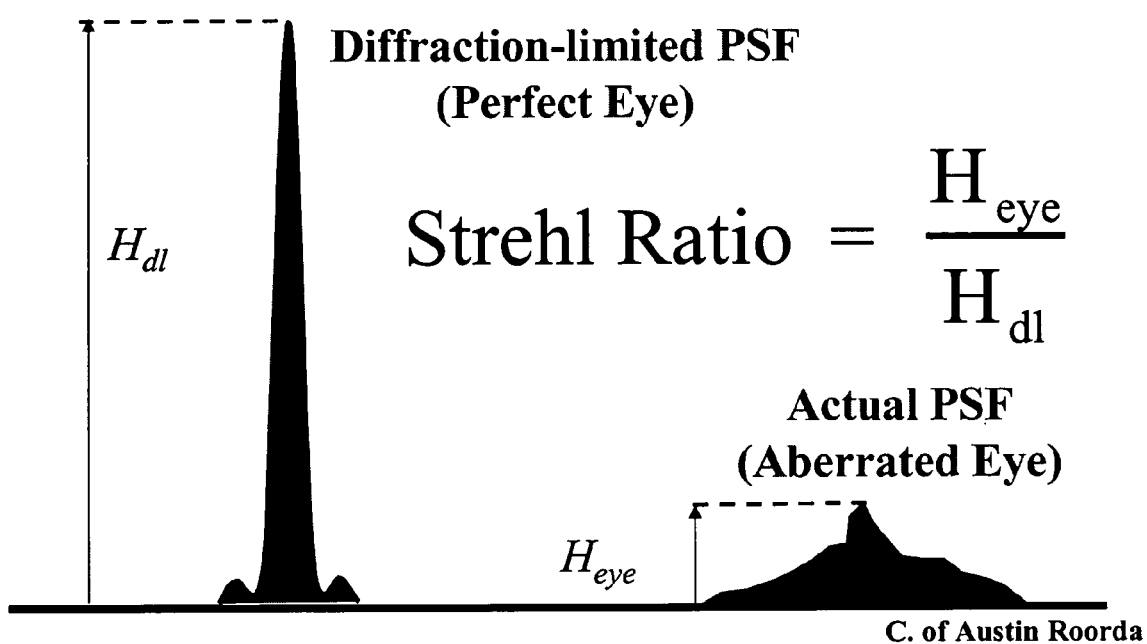
FIG. 9. The Strehl Ratio is equal to the maximum intensity in the PSF divided by the maximum intensity that would have been obtained in an optically perfect system. The range of possible values of Strehl Ratio is 0-1.

The common PSF metric based on the intensity of the PSF is the Strehl Ratio, (PS6), which is illustrated in FIG. 9. The Strehl Ratio is equal to the maximum intensity in the PSF divided by the maximum intensity that would have been obtained in an optically perfect system. The range of possible values of Strehl Ratio is 0-1. Strehl Ratio accounted for 54% of the variation in the acuity in blurred letter charts in the experiment of Applegate et al, in press, as shown in FIG. 7. Though this is better than the predictive power of RMS, it is not as good as the Pupil Fraction metric introduced earlier, which accounted for 64% of the variance.

Figure 10:
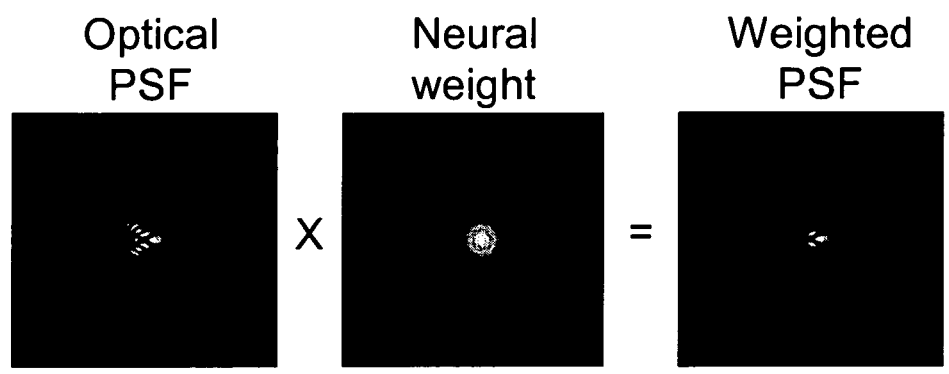
FIG. 10. Sharpness of the PSF is computed by multiplying the PSF by a Gaussian weighting function and summing the result. A similar metric called Visual Strehl uses a neural weighting function derived from the human contrast sensitivity function for interference fringes. On a scale of 0-1, Sharpness=0.35 and Visual Strehl=0.25 in this example (6 mm pupil, 0.25 µm coma)

The metric, which we have called Sharpness (PS10), illustrated in FIG. 10, includes a component intended to capture neural processing of the retinal image. Sharpness is the integral of the PSF multiplied by a Gaussian weighting function located in that retinal area over which the nervous system averages light. This averaging process is a form of neural blurring in addition to the optical blurring that is captured by the PSF alone. The total intensity in the weighted PSF indicates the compactness of the optical PSF. It is convenient to normalize this value by the corresponding value computed for an optically perfect eye so that the range of possible values of the Sharpness metric is 0-1.

Image Plane Metrics using the Optical Transfer Function: Another class of image plane metrics, which use the OTF, the Optical Transfer Function, is described below:

SF1=cutoff spatial frequency of radially-averaged modulation-transfer function (rMTF). Note that rMTF is not affected by the phase-transfer function (PTF) component of the OTF.

SF1=maximum spatial frequency for which rMTF>neural threshold where $$rMTF(f) = \int_0^{2\pi} \text{abs}(OTF(f, \phi))d\phi$$

and OTF(f,φ) is the optical transfer function for spatial frequency coordinates f (frequency) and φ (orientation).

SF2=area of visibility for rMTF (normalized to diffraction-limited case).

$$SF2 = \frac{\int_0^{cutoff} rMTF(f)df - \int_0^{cutoff} T_N(f)df}{\int_0^{cutoff} rMTF_{DL}(f)df - \int_0^{cutoff} T_N(f)df}$$

where $T_N$ is the neural contrast threshold function, which equals the inverse of the neural contrast sensitivity function.

SF3=cutoff spatial frequency of radially-averaged optical-transfer function (rOTF). Note that the phase-transfer function (PTF) component of the OTF is included when computing rOTF.

SF3=maximum spatial frequency for which rOTF>neural threshold where $$rOTF(f) = \int_0^{2\pi} OTF(f, \phi)d\phi$$

and OTF(f,φ) is the optical transfer function for spatial frequency coordinates f (frequency) and φ (orientation).

SF4=area of visibility for rOTF (normalized to diffraction-limited case).

$$SF4 = \frac{\int_0^{cutoff} rOTF(f)df - \int_0^{cutoff} T_N(f)df}{\int_0^{cutoff} rOTF_{DL}(f)df - \int_0^{cutoff} T_N(f)df}$$

where $T_N$ is the neural contrast threshold function, which equals the inverse of the neural contrast sensitivity function.

SF5=Strehl ratio computed in frequency domain (OTF method)

$$SF5 = \frac{\int_{-\infty}^{\infty}\int_{-\infty}^{\infty} OTF(f_x, f_y)df_x df_y}{\int_{-\infty}^{\infty}\int_{-\infty}^{\infty} OTF_{DL}(f_x, f_y)df_x df_y}$$

SF6=volume under OTF/volume under MTF $$SF6 = \frac{\int_{-\infty}^{\infty}\int_{-\infty}^{\infty} OTF(f_x, f_y)df_x df_y}{\int_{-\infty}^{\infty}\int_{-\infty}^{\infty} MTF(f_x, f_y)df_x df_y}$$

Note that this metric is designed to be sensitive to phase effects in the PTF.

SF7=visual Strehl ratio computed in frequency domain (OTF method)

$$SF7 = \frac{\int_{-\infty}^{\infty}\int_{-\infty}^{\infty} CSF_N(f_x, f_y) \cdot OTF(f_x, f_y)df_x df_y}{\int_{-\infty}^{\infty}\int_{-\infty}^{\infty} CSF_N(f_x, f_y) \cdot OTF_{DL}(f_x, f_y)df_x df_y}$$

Note that this metric differs from PS11 by revealing image quality at the coordinate origin, rather than at the peak of the PSF.

SF8=volume under neurally-weighted OTF/volume under neurally-weighted MTF $$SF8 = \frac{\int_{-\infty}^{\infty}\int_{-\infty}^{\infty} CSF(f_x, f_y) \cdot OTF(f_x, f_y)df_x df_y}{\int_{-\infty}^{\infty}\int_{-\infty}^{\infty} CSF(f_x, f_y) \cdot MTF(f_x, f_y)df_x df_y}$$

Note that this metric is designed to quantify phase effects in the PTF.

SF9=modified Strehl ratio (MTF method)

$$SF9 = \frac{\int_{-\infty}^{\infty}\int_{-\infty}^{\infty} MTF(f_x, f_y) df_x df_y}{\int_{-\infty}^{\infty}\int_{-\infty}^{\infty} MTF_{DL}(f_x, f_y) df_x df_y}$$

Note that Strehl ratio computed by MTF method is for a hypothetical PSF with even symmetry (i.e. PTF=0).

SF10=visual Strehl ratio computed in frequency domain (MTF method)

$$SF10 = \frac{\int_{-\infty}^{\infty}\int_{-\infty}^{\infty} CSF_N(f_x, f_y) \cdot MTF(f_x, f_y) df_x df_y}{\int_{-\infty}^{\infty}\int_{-\infty}^{\infty} CSF_N(f_x, f_y) \cdot MTF_{DL}(f_x, f_y) df_x df_y}$$

Note that this metric differs from PS11 by revealing image quality at the coordinate origin, rather than at the peak of the PSF.

One of these OTF related metrics, called Visual Strehl, introduced by Thibos and Applegate, uses the neural point-spread function as a neural weighting function. This neural PSF is equal to the inverse Fourier transform of the neural contrast sensitivity function for interference fringes. Interference fringes bypass the optical aberrations of the eye, thereby isolating the neural factors that determine visual sensitivity to patterns.

FIG. 7 shows the sharpness metric (PS10) applied to the data of Applegate et al. Sharpness accounts for 71% of the variance of Applegate et al.'s visual acuity data and Visual Strehl (SF7) accounts for 81% of the variance, which is more than the Pupil Fraction metric, the Strehl Ratio, or RMS Wave front Error. A number of variations of these metrics have been explored, all based on the premise of an image formation stage followed by a neural processing stage. As a practical matter, many of these variations are implemented more easily in the frequency domain (for grating images) instead of the spatial domain (for images of point sources). These metrics can also account for a large fraction of the variance in experimental data for a variety of visual tasks.

Figure 13:
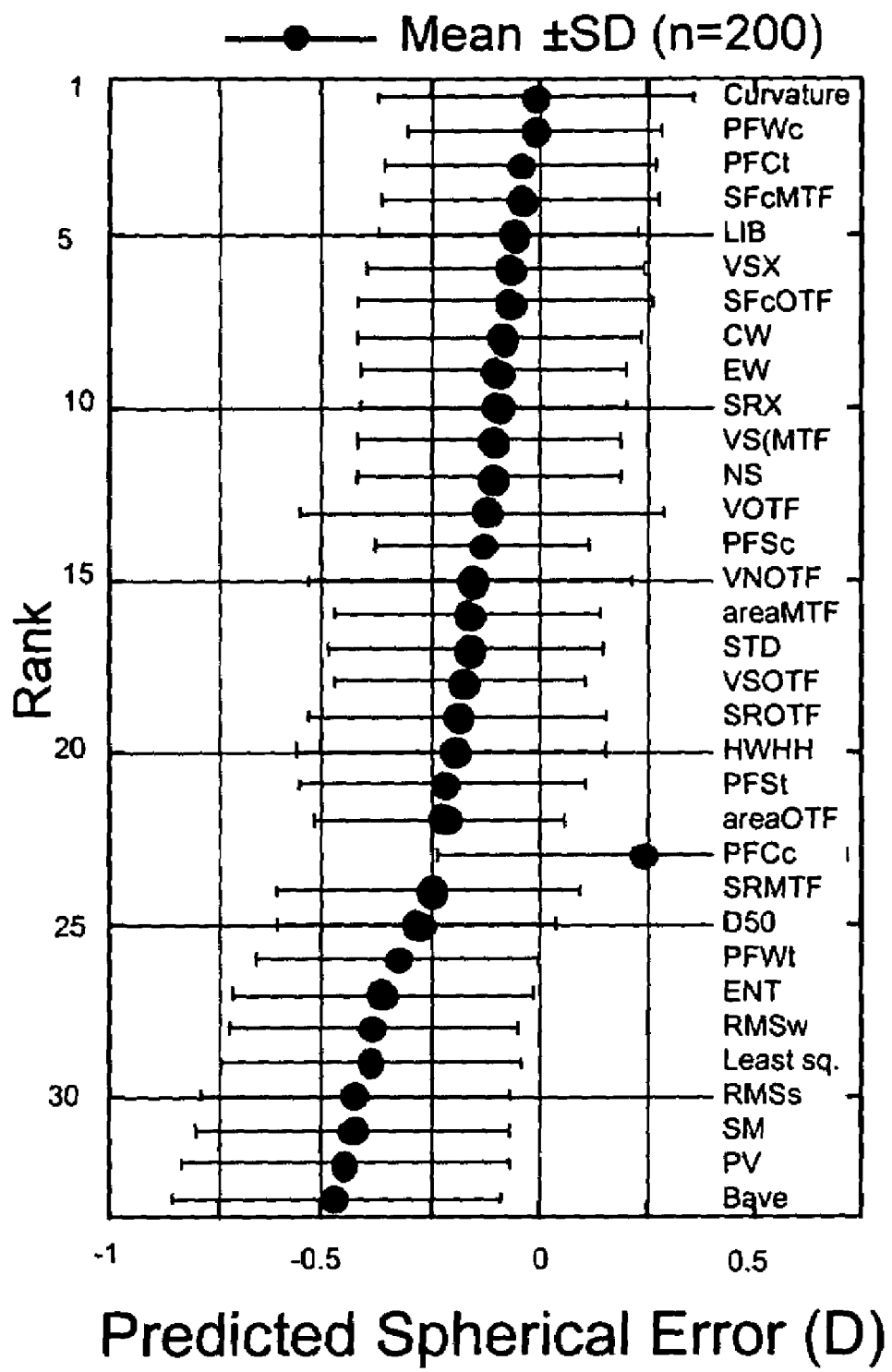
FIG. 13. Comparison of the accuracy of the proposed metrics.

FIG. 13 shows the rank ordering, based on accuracy, of 33 methods for predicting spherical refractive error. Error bars indicate the standard deviation of the population. The following are the abbreviations used:

| N | Acronym | Brief Description |
|---|---------|-------------------|
| 1 | RMSw | Standard deviation of wavefront |
| 2 | PV | Peak-valley |
| 3 | RMSs | RMSs: std(slope) |
| 4 | PFWc | Pupil fraction for wavefront (critical pupil) |
| 5 | PFWt | Pupil fraction for wavefront (tessellation) |
| 6 | PFSt | Pupil fraction for slope (tessellation) |
| 7 | PFSc | Pupil fraction for slope (critical pupil) |
| 8 | Bave | Average Blur Strength |
| 9 | PFCt | Pupil fraction for curvature (tessellation) |
| 10 | PFCc | Pupil fraction for curvature (critical pupil) |
| 11 | D50 | 50% width (min) |
| 12 | EW | Equivalent width (min) |
| 13 | SM | Sqrt(2nd moment) (min) |
| 14 | HWHH | Half width at half height (arcmin) |
| 15 | CW | Correlation width (min) |
| 16 | SRX | Strehl ratio in space domain |

-continued

| N | Acronym | Brief Description |
|---|---------|-------------------|
| 17 | LIB | Light in the bucket (norm) |
| 18 | STD | Standard deviation of intensity (norm) |
| 19 | ENT | Entropy (bits) |
| 20 | NS | Neural sharpness (norm) |
| 21 | VSX | Visual Strehl in space domain |
| 22 | SFcMTF | Cutoff spat. freq. for rMTF (c/d) |
| 23 | AreaMTF | Area of visibility for rMTF (norm) |
| 24 | SFcOTF | Cutoff spat. freq. for rOTF (c/d) |
| 25 | AreaOTF | Area of visibility for rOTF (norm) |
| 26 | SROTF | Strehl ratio for OTF |
| 27 | VOTF | OTF vol/MTF vol |
| 28 | VSOTF | Visual Strehl ratio for OTF |
| 29 | VNOTF | CS*OTF vol/CS*MTF vol |
| 30 | SRMTF | Strehl ratio for MTF |
| 31 | VSMTF | Visual Strehl ratio for MTF |
| 32 | LSq | Least squares fit |
| 33 | Curve | Curvature fit |

Another aspect of the invention will now be disclosed. That aspect is a generalization of the "equivalent sphere" concept, which sought to represent a wavefront with a sphere. In the present invention, the equivalent sphere is generalized to an "equivalent quadratic," which represents any wavefront with a quadratic (i.e., spherico-cylindrical) surface.

We define the equivalent quadratic of a wavefront aberration map as that quadratic (i.e. a sphero-cylindrical) surface which best represents the map. This idea of approximating an arbitrary surface with an equivalent quadratic is a simple extension of the common ophthalmic technique of approximating a sphero-cylindrical surface with an equivalent sphere. Two methods for determining the equivalent quadratic from an aberration map are presented next.

One common way to fit an arbitrarily aberrated wavefront with a quadratic surface is to minimize the sum of squared deviations between the two surfaces. This least-squares fitting method is the basis for Zernike expansion of wavefronts. Because the Zernike expansion employs an orthogonal set of basis functions, the least-squares solution is given by the second-order Zernike coefficients, regardless of the values of the other coefficients. These second-order Zernike coefficients can be converted to a sphero-cylindrical prescription in power vector notation using eqns (1).

$$M = \frac{-c_2^0 4\sqrt{3}}{r^2} \tag{1}$$

$$J_0 = \frac{-c_2^2 2\sqrt{6}}{r^2}$$

$$J_{45} = \frac{-c_2^{-2} 2\sqrt{6}}{r^2}$$

where $c_n^m$ is the $n^{th}$ order Zernike coefficient of meridional frequency m, and r is pupil radius. The power vector notation is a cross-cylinder convention that is easily transposed into conventional minus-cylinder or plus-cylinder formats used by clinicians (see eqns 22, 23 of Thibos, Wheeler, & Horner, 1997).

The other method to be presented is paraxial curvature fitting. Curvature is the property of wavefronts that determines how they focus. Thus, another reasonable way to fit an arbitrary wavefront with a quadratic surface is to match the curvature of the two surfaces at some reference point. A variety of reference points could be selected, but the natural choice is the pupil center. Two surfaces that are tangent at a point and have exactly the same curvature in every meridian are said to osculate.

Thus, the surface we seek is the osculating quadric. Fortunately, a closed-form solution exists for the problem of deriving the power vector parameters of the osculating quadratic from the Zernike coefficients of the wavefront. This solution is obtained by computing the curvature at the origin of the Zernike expansion of the Seidel formulae for defocus and astigmatism. This process effectively collects all $r^2$ terms from the various Zernike modes. We used the OSA definitions of the Zernike polynomials, each of which has unit variance over the unit circle. The results given in equation (2) are truncated at the sixth Zernike order but could be extended to higher orders if warranted.

$$M = \frac{-c_2^0 4\sqrt{3} + c_4^0 12\sqrt{5} - c_6^0 24\sqrt{7} + \ldots}{r^2}$$

$$J_0 = \frac{-c_2^2 2\sqrt{6} + c_4^2 6\sqrt{10} - c_6^2 12\sqrt{14} + \ldots}{r^2}$$

$$J_{45} = \frac{-c_2^{-2} 2\sqrt{6} + c_4^{-2} 6\sqrt{10} - c_6^{-2} 12\sqrt{14} + \ldots}{r^2}$$

(2)

Figure 14:
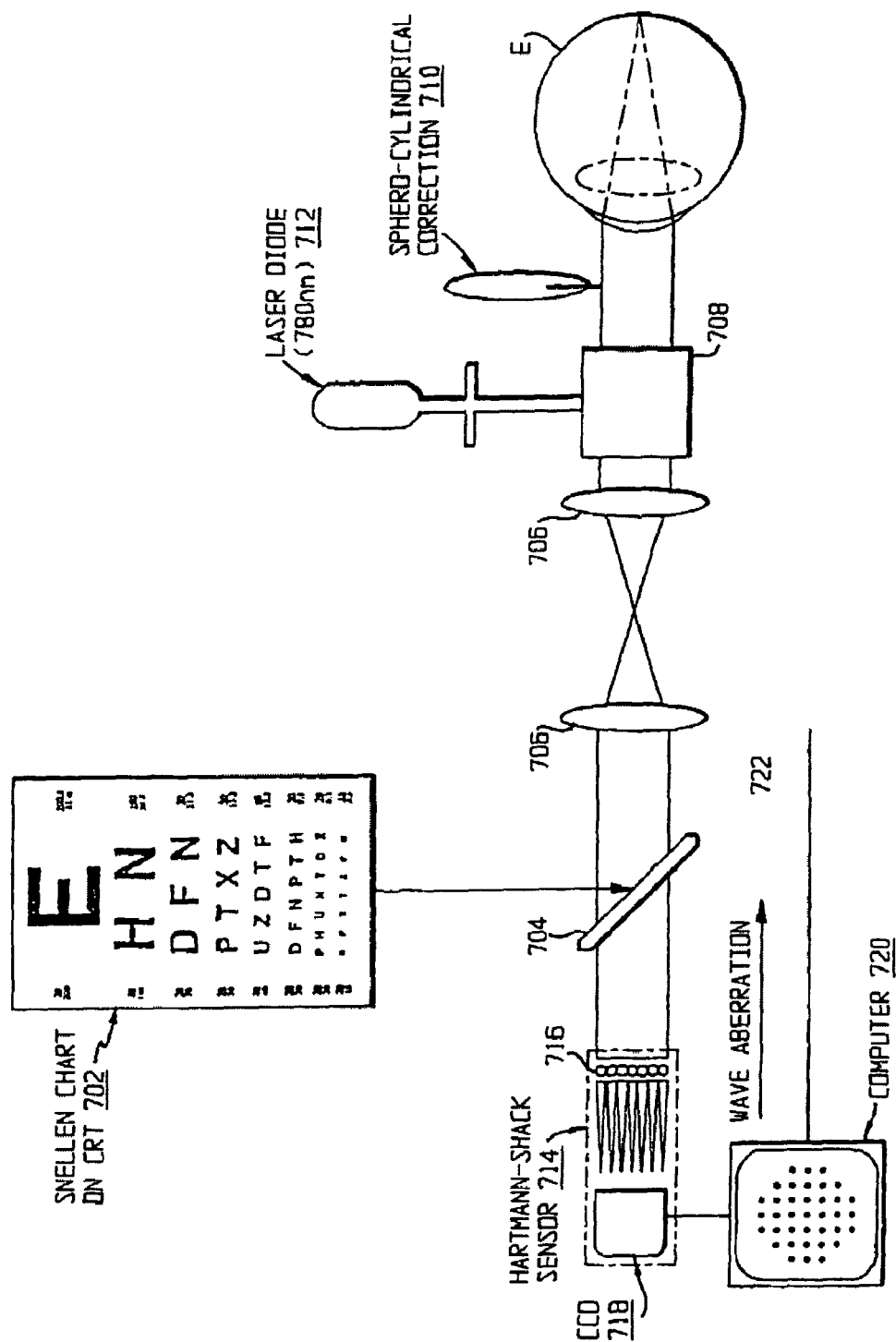
FIG. 14. An example of a system on which the present invention can be implemented.

Any embodiment of the present invention can be implemented in a device such as that shown in FIG. 14, which is reproduced from FIG. 7 of U.S. Pat. No. 6,511,180. Other devices will suggest themselves to those skilled in the art; therefore, the device of FIG. 7 is meant as illustrative rather than limiting. The apparatus is based on a Shack-Hartmann sensor, which is well known in the art. The subject sees through the system a Snellen chart presented on a CRT. The subjective refraction and the wave aberration measurements are performed under the same conditions.

More specifically, in the system 700 of FIG. 14, the subject is shown a Snellen chart 702 on a CRT, an LCD screen, or a similar device. Alternatively, the Snellen chart can be printed, or another chart can be used. The Snellen chart 702 is imaged through a beamsplitter 704, a conjugate lens system 706, another beamsplitter 708, and optionally a removable sphere-cylindrical correction system 710 onto the retina of the subject's eye E. Light from a laser diode 712 is directed through the beamsplitter 708 onto the retina of the subject's eye E. The light from the laser diode 712 reflected from the retina passes through the beamsplitter 708, the conjugate lens system 706 and the beamsplitter 704 into a Shack-Hartmann sensor 714, which includes a lenticular array 716 and a CCD or other photodetector array 718. The Shack-Hartmann sensor 714 produces an output which is directed to a computer 720. A widely-available Pentium III-class computer suffices. The output can be supplied to a lens fabrication, surgical correction, adaptive optics, or image simulation system 722, which can prepare a spectacle lens, a contact lens, or an intraocular lens to correct the eye's wave aberration, control a surgical technique upon the eye E to correct the aberration, provide adaptive optics such as a deformable mirror to provide a counter-aberration, or simulate an image showing how the subject would view a scene after correction of aberrations.

Figure 12:
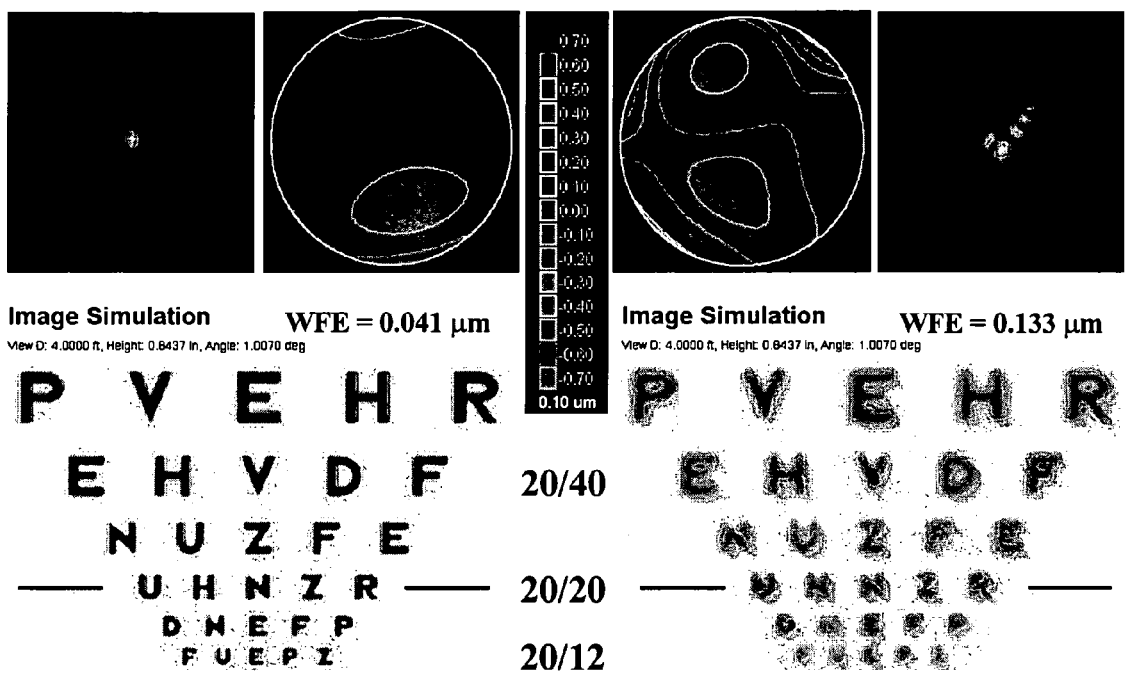
FIG. 12. Two different wave aberrations for which high-contrast visual acuity was the same (20/15) but subjective image quality was quite different. In this case, the value of a metric based on visual acuity would be different than the value of a metric based on a judgment of subjective image quality. Best spectacle correction, 3 mm pupil diameter. Eye on left is for a typical, non-surgical eye. Eye on right is for a successful, post-LASIK patient after 1 yr. The computed PSFs, wave front error maps, and simulations of the retinal image were computed with CTView, by Sarver & Associates (www.sarverassociates.com).

Task Dependence. One of the fundamental difficulties in choosing an optimum metric is that it is highly dependent on the visual task. For example, a task that requires detecting relatively large features in a low contrast environment would demand a quite different metric than detecting tiny features at very high contrast. Other factors associated with the task can influence the optimum metric, such as luminance, pupil size, and object distance. FIG. 12 shows an example of two different wave aberrations that have approximate equivalence in visual acuity, as measured by the simple ability to read letters on an eye chart, but quite different subjective image quality. In this case, a metric based on visual acuity would be different than a metric based on a judgment of subjective image quality.

Fully-Automated Refraction. Autorefractors have not replaced subjective refraction as the ultimate method to prescribe vision correction. The advent of wave front sensing reopens the possibility of fully automated and improved refraction. This is because wave front sensors provide much more information than conventional autorefractors, since they indicate the fate of light as it passes through every point in the pupil. A consortium of investigators from Lawrence Livermore National Laboratories, University of Rochester, Bausch and Lomb, Wave front Sciences, and Sandia National Laboratories has developed a compact phoropter equipped with adaptive optics. This device, which incorporates a wave front sensor, can provide a refraction and/or a prescription for correcting higher order aberrations in a fraction of a second. The incorporation of a deformable mirror also allows subjective image quality to be assessed with any of a broad range of customized vision corrections. Metrics of the kind here discussed will be required to find the endpoint of refraction based on a variety of criteria before choosing the best-customized correction. Guirao and Williams (2002) describe a fast algorithm to compute the optimum vision correction for any metric from wave aberration data. Coupled with a biologically-plausible metric designed to mimic the eye and brain of each patient, wave front sensors may ultimately surpass the clinical refraction as the preferred method for choosing the best correction, whether the correction is implemented with refractive surgery, spectacles, contact lenses, intraocular lenses, or any other method. Thibos, Applegate, and Bradley, U.S. Provisional Patent Application No. 60/529,357, filed Dec. 12, 2003, entitled "System and Method for Optimizing Clinical Optic Prescriptions," whose disclosure is hereby incorporated by reference in its entirety into the present disclosure, have disclosed a simplified search method.

Principles for Constructing a Metric. The purpose of incorporating an image quality metric into a wave front sensor is to summarize the visual impact of each patient's wave aberration. Unfortunately, the number of metrics that one might explore is large. To make this problem tractable, the search must be restricted to those domains that are most likely to yield the best solutions. Therefore, we have developed a metric using biological plausibility as the criterion for restricting the search for good metrics of image quality. That is, we have developed a fast algorithm that mimics those steps that the patient's eye and brain actually take in order to see. The more realistically the model captures the processing stages in the human visual system, the more successful the metric will be. For example, the optics of the eye forms a retinal image through a process that is well understood and can be accurately described mathematically. The retinal image is then processed by a nervous system, the properties of which are also reasonably well understood. Another strength of building the metric around a model of vision is that additional factors can be added to the model as their significance is assessed. For example, the model might initially incorporate only blur from aberrations and neural blur.

It seems highly likely that improvements in metric performance will be realized by building additional features into the model of human vision. For example, it is known that the eye is less sensitive to edges at oblique orientations than to those oriented horizontally or vertically, and a metric that incorporated that feature might perform better than the isotropic metrics we have implemented so far. As the model develops, incorporating factors such as the Stiles-Crawford effect, light scatter, and/or neural plasticity should increase predictive power.

The Stiles-Crawford effect, which is accounts for the observation that light passing through the periphery of a pupil does not appear as bright as light passing through the pupil near the center, could be built into a model using a point spread function PSF(λ) of the form:

PSF(λ)=|FT$^{-1}${A(x,y)exp(iW(x, y, λ)}|$^2$ where A(x,y)=exp(-ρ(x$^2$+y$^2$)) is the Stiles-Crawford apodization function. Other weighting functions in the pupil plane could also be used. All of the metrics would be modified accordingly.

Figure 11:
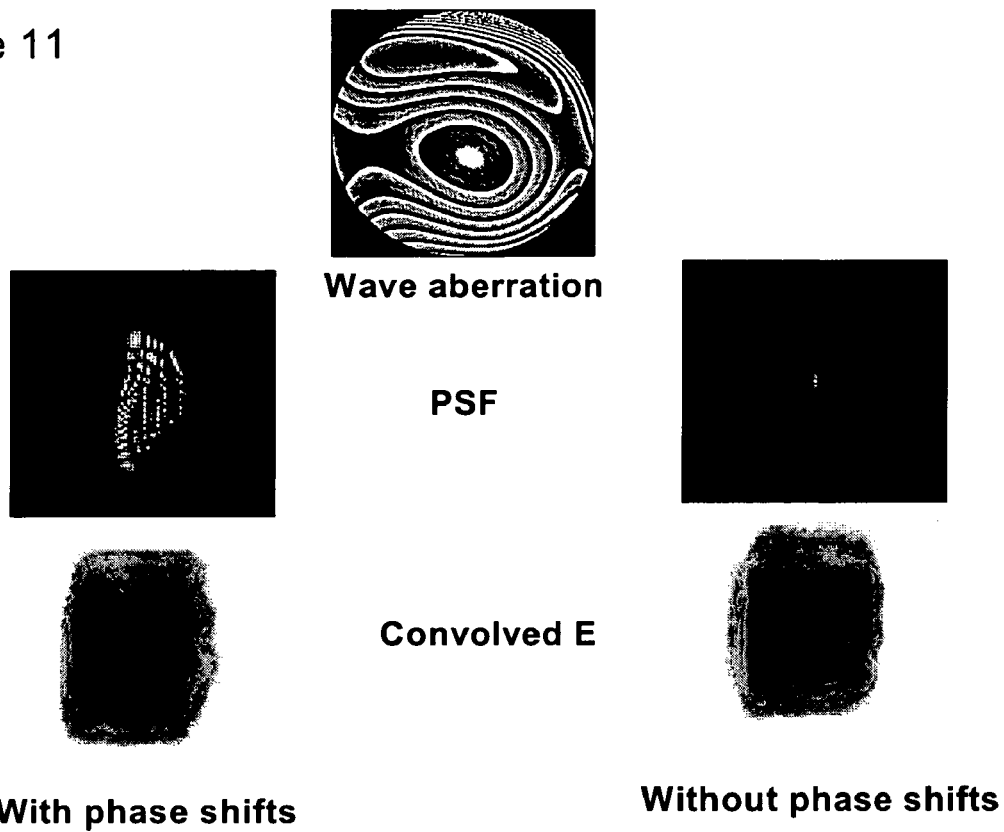
FIG. 11. The importance of phase fidelity. The wave aberration of a post-Lasik patient (top) was used to compute the PSF (middle left) which was then convolved with the letter E to simulate the retinal image (bottom left). The calculation was then repeated assuming zero phase shifts to produce a much improved PSF (middle right) and consequently an improved retinal image of the letter E (bottom right). The letter subtended 40' of arc.

Phase Shifts: Any failure to preserve these spatial relations is called a phase shift. The phase transfer function describes the phase shift for all possible grating components (spatial frequency). A perfect optical system produces no phase shifts, but the real eye is not perfect in this respect, especially when the pupil is large. It is well known that changes in the phase spectrum of an image can often be more disruptive than changes in image contrast. The importance of phase fidelity is illustrated in FIG. 11 which shows the wave aberration of a post LASIK patient, the PSF with and without phase shifts, and the convolution of the PSF with the letter E. Note the difference in the retinal image when phase shifts are included. The best metrics will include the phase shifts that the eye's optics can introduce.

Polychromatic Metrics: The metrics we have described to date are defined for a single wavelength of light. However, the world is composed of objects that generally reflect all wavelengths of light, albeit by different amounts. The retinal image quality depends on the spectral nature of light because of chromatic aberration in the eye. Our image plane metrics can be generalized to include chromatic aberration and this is important because chromatic aberration interacts with the eye's monochromatic aberrations in determining the overall image quality. The polychromatic point-spread function $PSF_{poly}$ is defined as $$PSF_{poly} = \int_\lambda S(\lambda) \cdot PSF(x, y, \lambda) d\lambda$$

where S(λ) is the luminance spectrum of the source.

The polychromatic optical-transfer function $OTF_{poly}$ is defined as $OTF_{poly}$=FT{$PSF_{poly}$} where FT means Fourier transform.

More generally, it is possible to compute the value of a given metric for each wavelength and to form a weighted average of the results:

$Metric_{poly}$=∫V(λ)Metric(λ)dλ where the weighting function V(λ) is the luminous efficiency function that describes how visual sensitivity to monochromatic light varies with wavelength λ.

Pupil Size Normalization: The metrics we have devised to date are generally normalized to the ideal optical system for the same pupil size. This is a good way to formulate the metric to determine how sharp the image is compared with the sharpest it could be for that particular pupil size. In other circumstances, it is useful to develop a metric that is robust across all pupil sizes. The advantage of such a metric is that it captures the absolute quality of vision regardless of the pupil size.

Multivariate Metrics: The metrics described here are univariate: only one number is used to describe image quality. However, loss of image quality can arise from multiple causes that are perceptually distinct. For example, image quality declines when edges become blurred, but also when the overall contrast of the image is reduced. Alternatively, flaring in a particular direction or multiple ghost images can greatly reduce image quality and visual performance. A combination of metrics, each of which is sensitive to a different aspect of image quality is superior to any single metric on its own and would provide the clinician with an indication of how the retinal image is disrupted. For example, a retinal image with a strong flare in one direction could not be distinguished from a retinal image that suffered from an equivalent amount of symmetric blur. However, this would be revealed by a metric sensitive to the symmetry of the point spread function. One strategy is to adopt a tripartite metric with separate numbers for contrast, sharpness, and symmetry in the retinal image. Even a tripartite scheme may not be sufficient to capture the important variations that can arise in the eye's PSF. For example, multiple ghost imagery could require a fourth metric. The number of metrics adopted is a compromise between simplicity and accuracy.

Population Norms: The metrics as defined above and as used for comparison to subjective refraction data have been normalized to a range of 0 to 1. For the purpose of communicating vision quality to a patient, these metric values are to be converted into scores that reflect population norms. For example, if the metric were transformed to a percentile, the clinician knows what fraction of the patient population has worse optics than the patient in question. A similar consideration is self-normalization, which is a normalization based on one or more prior examinations on the same patient.

Adaptability (Plasticity) of Human Neural Processing: Metrics also need to incorporate the fact that neural processing is plastic, changing its performance depending on the wave aberration used to view the world. There is a long history of research revealing neural plasticity. Distortions in the visual field, introduced with prisms, appear to disappear with time, as do the chromatic fringes caused by chromatic aberration, because the neural processing accommodates to the distortion. Recent experiments by Pablo Artal, working with Williams reveal that this plasticity extends to the monochromatic aberrations of the eye as well. Artal used the Rochester Adaptive Optic System to remove the wave aberration from a subject. He then replaced the wave aberration, either in its original orientation or rotated by some amount. Despite the fact that the rotation only changes the orientation of the aberrations and not the objective amount of retinal blur, the subjective blurchanged dramatically. Subjects viewing the world through their own wave aberration reported that it was much sharper than when the wave aberration was rotated. These observations support clinical wisdom that patients will often reject astigmatic corrections that improve image quality, but cause too large a departure from their normal experience of the world. The effect has far-reaching implications for vision correction, since it means that subjects who receive an aberration-free view of the world through customized correction may require time to adjust to the benefit. Alternatively, vision correction might best be accomplished through a multiple step process that ultimately converges on the desired correction.

Metric Customization: Though the development and validation of metrics based on the typical patient is the obvious first goal, the metrics might also be customized depending on the specific needs and characteristics of each patient. For example, older patients are likely to have more light scatter, their pupil sizes are smaller on average, their accommodation range is reduced, and they will probably tolerate large changes in vision correction less readily. A metric that includes patient age as a parameter helps to ensure the optimum vision correction. For example, the optimum metric for someone with poor neural contrast sensitivity will be different than the metric for someone with exquisite neural sensitivity. It is possible to build known features of an individual patient's nervous system into the metric. For example, with laser interferometry or adaptive optics, it is possible to measure the neural performance of the eye independent of its optical quality. There are large variations in the neural performance of normal eyes and the metric can be customized to each patient accordingly. One can also customize the metric based on lifestyle. For example, patients with reduced accommodation or whose lifestyle requires good focus over a large range of viewing distances might benefit from a increase in spherical aberration compared with a patient, such as a pilot, who would prefer to optimize performance at infinity. Any metric needs to incorporate the depth of field of the eye and how it varies with pupil size, accommodation, and aberrations to correct the eye in such a way as to maximize the range of viewing distances over which optical-quality is acceptable; this matter will be explained below with reference to the hyperfocal distance. It is well known that some patients prefer a "softer" image than others and a customized metric may offer patients a choice along this or other esthetic dimensions.

Hyperfocal distance: It is possible to correct a refraction estimate for hyperfocal distance. Hyperfocal distance is defined as the nearest distance on which the retina can focus without significantly reducing visual performance for a target located at infinity. As shown in the lower half of FIG. 15, in conventional correction, the user's vision can be corrected to conjugate the fovea of the eye with the hyperfocal point, which is a point at the hyperfocal distance. The distance labeled DOF is called the depth of focus. Both the DOF and the hyperfocal distance are related to the patient's natural pupil size, which can thus be taken into account in performing the calculations.

Figure 15:
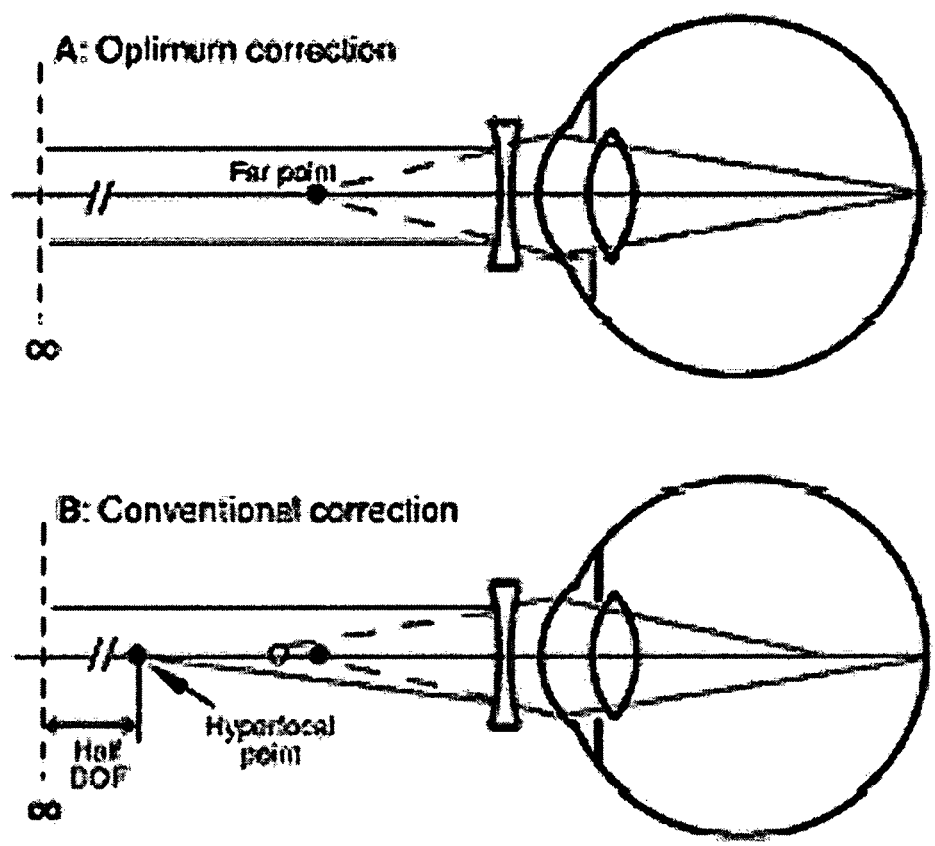
FIG. 15. A comparison between optimal and conventional correction.

A source of systematic bias in objective refraction may be attributed to the difference between optimal and conventional refraction methods. The objective refraction procedures described in this disclosure are designed to determine the optimum refraction (FIG. 15, top) whereas the subjective refractions were conventional (FIG. 15, bottom). The difference between the two end-points is half the depth-of-focus (DOF) of the eye. The DOF for subjects in the Indiana Aberration Study is unknown, but we would anticipate a value of perhaps ±0.25 D, which is about half the total range of focus values spanned in FIG. 13. Accordingly, we may account for the results in FIG. 13 by supposing that the curvature matching technique happens to locate the far end of the DOF interval (which is located at optical infinity in a conventional refraction) whereas some middle-ranking metric (such as VSOTF) locates the middle of the DOF, located at the hyperfocal distance. This inference is consistent with the fact that most eyes in the Indiana Aberration Study had positive spherical aberration. Such eyes have less optical power for paraxial rays than for marginal rays. Consequently, the retina will appear to be conjugate to a point that is beyond the hyperfocal point if the analysis is confined to the paraxial rays.

The preceding arguments suggest that the superior accuracy of the curvature method for determining the spherical equivalent of a conventional refraction is due to a bias in this method that favors the far end of the eye's DOF. In short, curvature matching (and several other metrics with similar accuracy) is a biased method that successfully predicts a biased endpoint. By the same argument, the biased curvature method is not expected to predict astigmatism accurately because conventional refractions are unbiased for astigmatism. An objective wavefront analysis that accurately determines the hyperfocal point and the DOF with reduced variability could become the new gold standard of refraction. A refraction estimate can be corrected to for the hyperfocal distance.

While preferred embodiments of the present invention and modifications thereof have been presented, those skilled in the art will readily appreciate that other embodiments can be realized within the scope of the present invention. For example, when a metric is disclosed as a square root, another function can be used instead. Also, numerical values, such as a 50% cutoff, are illustrative rather than limiting. Furthermore, use of metrics is not limited to spherocylindrical refractive corrections, but may include estimating higher—order corrections, visual quality, and predicting visual performance on visual tasks (e.g. face recognition, visual acuity). Therefore, the present invention should be construed as limited only by the appended claims.

We claim:

1. A method for determining a metric to predict a subjective impact of aberrations in an eye of a patient, the method comprising:
    (a) receiving data signals representing the aberrations;
    (b) forming a wavefront aberration map from the data signals;
    (c) fitting a sphero-cylindrical or higher order surface to the wavefront aberration map by paraxial curvature fitting such that the sphero-cylindrical or higher order surface and the wavefront aberration map osculate; and
    (d) determining the metric from the sphero-cylindrical or higher order surface such that the metric predicts the subjective impact of the aberrations in the eye of the patient.

* * * * *